United States Patent [19]

Picard et al.

[11] Patent Number: 5,442,674
[45] Date of Patent: Aug. 15, 1995

[54] DEVICE AND AUTOMATIC METHOD FOR THE GEOMETRICAL CALIBRATION OF AN X-RAY IMAGING SYSTEM

[75] Inventors: Catherine Picard, Boulogne; Anne Rougee; Yves Trousset, both of Palaiseau, all of France

[73] Assignee: GE Medical Systems, Buc, France

[21] Appl. No.: 186,385

[22] Filed: Jan. 21, 1994

[30] Foreign Application Priority Data

Jan. 27, 1993 [FR] France .................... 93 00804

[51] Int. Cl.⁶ .................................. A61B 6/00
[52] U.S. Cl. ................................. 378/20; 378/18; 378/207
[58] Field of Search ............ 378/4, 18, 19, 20, 204, 378/207, 163

[56] References Cited

U.S. PATENT DOCUMENTS

| | | |
|---|---|---|
| 3,509,337 | 4/1970 | De Clerk et al. |
| 3,657,534 | 4/1972 | De Clerk et al. ............... 378/207 X |
| 4,344,183 | 8/1982 | Jacobson ............................. 378/207 |
| 4,818,943 | 4/1989 | Chandra ......................... 378/207 X |
| 4,984,160 | 1/1991 | Saint Felix et al. ............. 364/413.19 |
| 5,095,521 | 3/1992 | Trousset et al. .................... 395/121 |
| 5,123,037 | 6/1992 | Picard et al. ......................... 378/99 |
| 5,149,965 | 9/1992 | Marks ............................. 378/207 X |
| 5,218,534 | 6/1993 | Trousset et al. ............... 364/413.17 |
| 5,241,471 | 8/1993 | Trousset et al. ............... 364/413.19 |
| 5,299,253 | 3/1994 | Wessels ............................. 378/20 X |

FOREIGN PATENT DOCUMENTS

| | | |
|---|---|---|
| 1477825 | 3/1967 | France . |
| 2631810 | 12/1989 | France . |
| WO91/01071 | 1/1991 | France . |
| 621107 | 5/1949 | United Kingdom . |

*Primary Examiner*—David P. Porta
*Attorney, Agent, or Firm*—Nilles & Nilles

[57] ABSTRACT

A phantom constituted by a helix is used. This helix enables an automatic geometrical calibration of any X-ray imaging system that uses a plane detector.

23 Claims, 3 Drawing Sheets

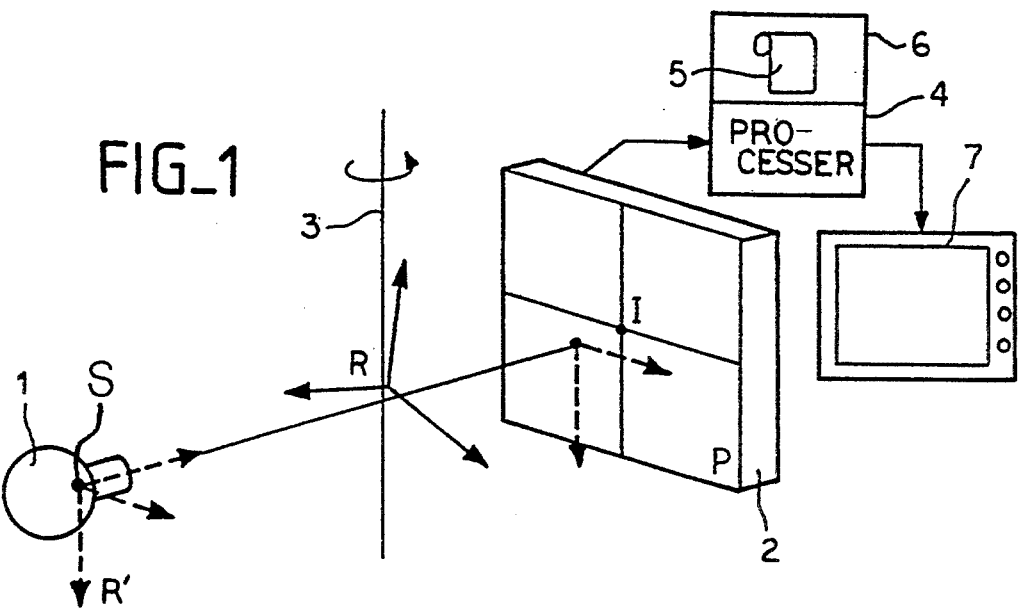
FIG_1
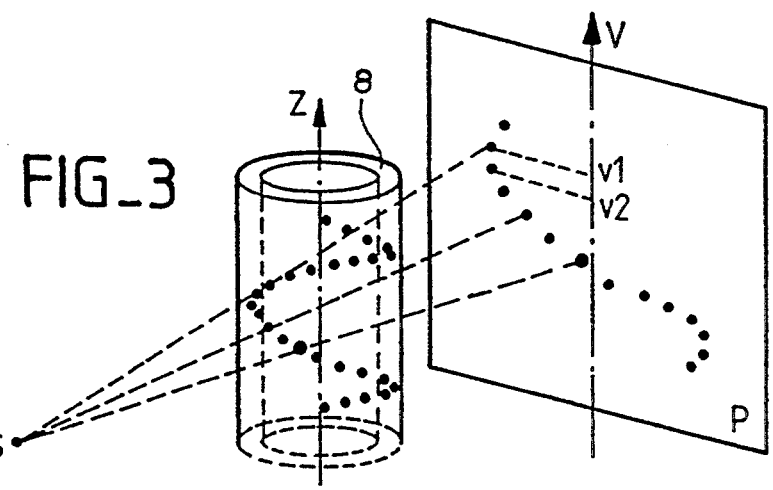
FIG_3
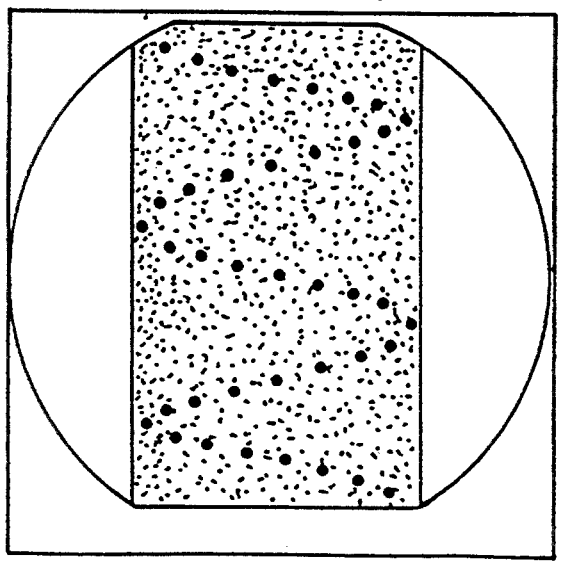
FIG_4a
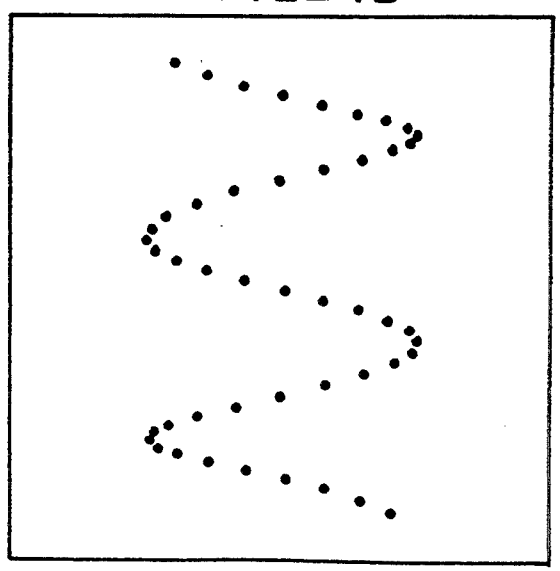
FIG_4b

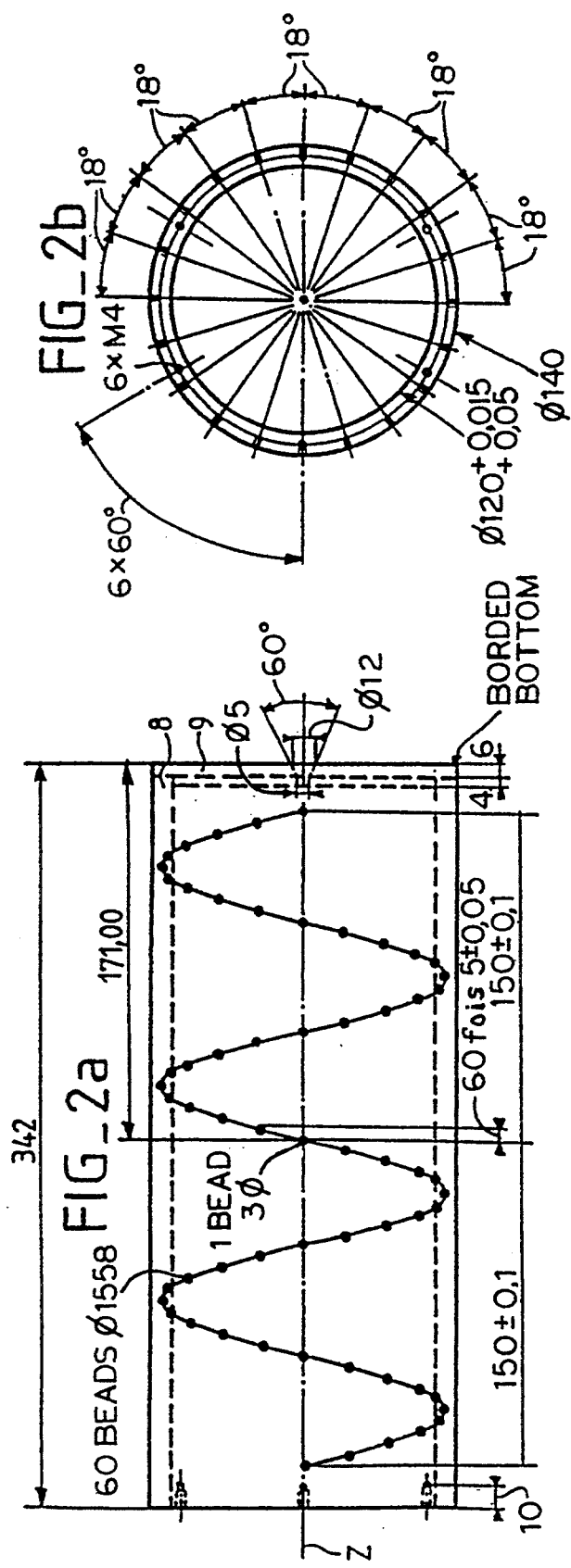
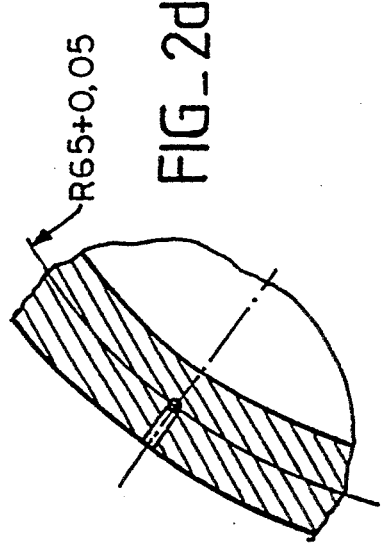
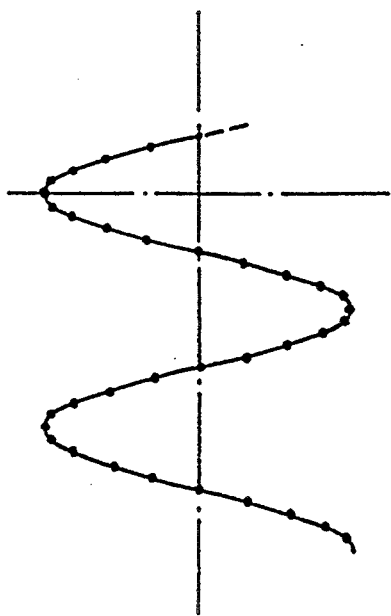

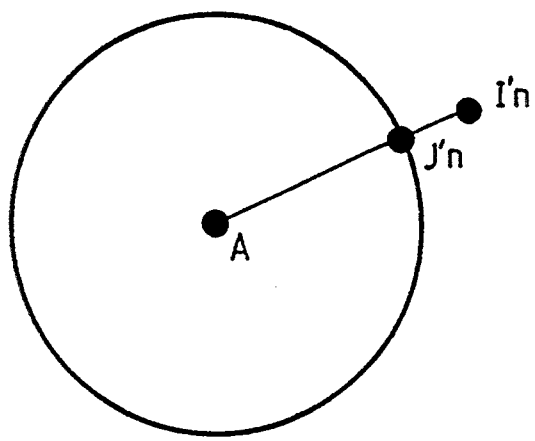
FIG_5a
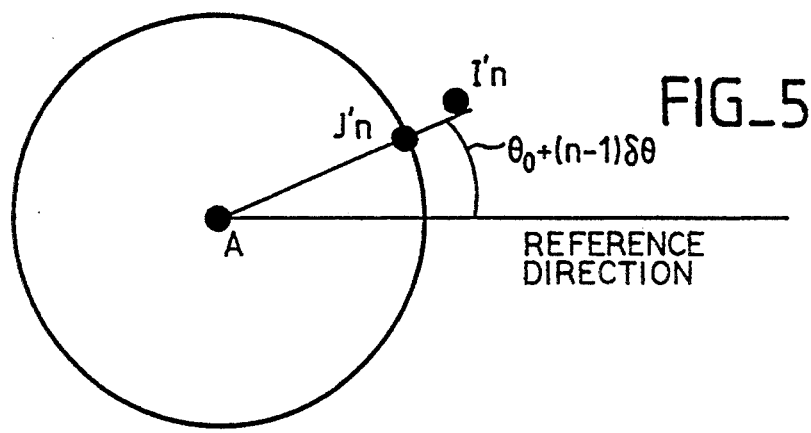
FIG_5b
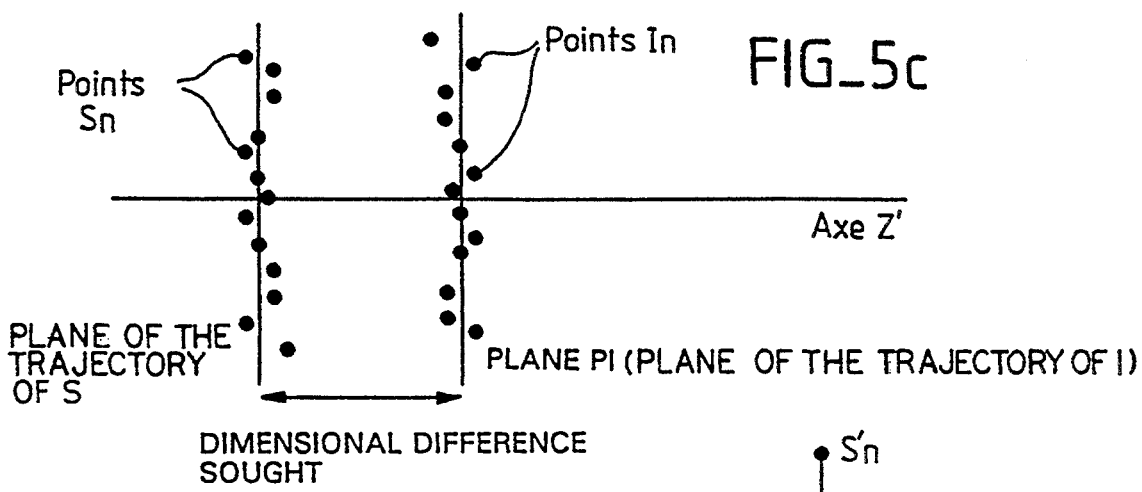
FIG_5c
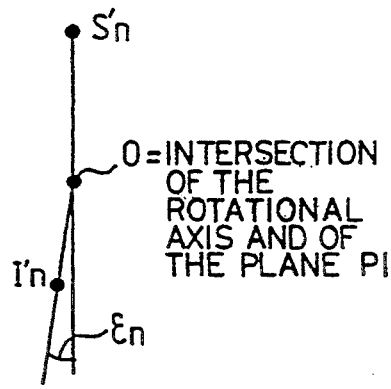
FIG_5d

DEVICE AND AUTOMATIC METHOD FOR THE GEOMETRICAL CALIBRATION OF AN X-RAY IMAGING SYSTEM

BACKGROUND OF THE INVENTION

1. Field of the Invention

The present invention relates to a device and to an automatic method for the geometrical calibration of an X-ray imaging system. Systems of this type are used chiefly in the medical field in order to analyze internal structures of the human body, notably vascular structures. The aim of the invention is to enable the use of the system, by means of its easy calibration, for the quantitative assessment and, qualitative assessment of the dimensions of the internal structres analyzed. The invention relates essentially to systems using 2D radiation detectors, for example substantially plane radiation detectors. The invention also pertains to a method of rotating systems of X-ray imaging.

2. Description of the Prior Art

In an X-ray imaging system formed by an X-ray source and a 2D detector, whether rotating or not, the geometrical operation that plays a role in the production of the image is a conical projection of an analyzed 3D object on a 2D space which is that of the plane of projection corresponding to the plane of detection. The geometrical parameters that completely describe the conical projection are nine in number. These nine parameters may be presented according to different types of parametrization.

The following is one of the possible types of parametrization:

three first parameters relate to the three coordinates of the X-ray source S in the referential system R of the 3D space in which the analyzed object is placed;

three other parameters relate to the three Euler's angles associated with the change of referential system between the referential system R of the 3D space of the object and a referential system R' related to the conical projection, i.e. a referential system formed by a 2D referential system of the plane of projection P and a third axis orthogonal to the plane of projection;

three last parameters relate to the three coordinates of an arbitrary point I of the plane of projection P (for example the center of the image in the referential system R).

To simplify the computations in the invention, it will be seen here below that there are reasons to prefer cylindrical coordinates for the first three and the last three coordinates. The referential system R is then a cylindrical referential system.

Knowledge of all or a part of these parameters is very often useful in radiology, notably when a quantitative data element pertaining to a 3D object is estimated from a measurement made in a 2D projection or in several 2D projections of this object. Parameters of each viewpoint must then be known. A viewpoint pertains to the orientation of the system with respect to the object. For example, we may take the standard problem of the estimation of the section of a vessel from one or more 2D projections. Now, gaining access to these parameters directly, i.e. for example by making direct measurement, on the acquisition system, of the distance between the X-ray source and the detector, is impossible or implies an excessive degree of imprecision.

The term "geometrical calibration of an imaging system" denotes the operation that leads to precise indirect knowledge of the geometrical parameters that play a role in the production of an image. The principle, which is a classic one, is based on the use of a geometrical phantom that is known in the 3D space and whose 2D projection is acquired. The sequence of the operations carried out to this end comprises the following steps:

a known object is available, namely a calibration phantom having a certain number of characteristic points whose position in space is known by coordinates measured with respect to a referential system proper to this object;

the image of this phantom is acquired under the geometrical conditions of a viewpoint (or incidence) that is to be calibrated;

the projections of the characteristic points in the image are recognized. For this purpose, each characteristic point of the object is associated with its trace in the acquired image, namely the projection;

the system of equations describing the projection is inverted in the mathematical sense;

and, finally, all of the parameters of the projection for the given viewpoint are obtained.

In the prior art, the recognition of the characteristic points in the projection of the calibration phantom is done "by hand" by a human operator. For example, a frequently used form of geometrical calibration phantom is that of a cube, at the eight corners of which metal beads or bullets, opaque to light, are positioned. Sometimes, supplementary beads are added on to increase the geometrical precision of the calibration. Now, projection along the direction of the X-rays produces a "transparent" image of the object wherein, depending on the orientation of the tube, it may be very difficult to associate the 2D traces of the beads with their corresponding 3D points without making mistakes. The following articles may be referred to for the state of the art as regards geometrical calibration:

(1) D. L. Parker, J. Wu, D. L. Pope, R. Van Bree, G. R. Caputo and H. W. Marshall, "Three-Dimensional Reconstruction And Flow Measurements of Coronary Arteries Using Multiview Digital Angiography", in J. C. Reiber and P. W. Serruys ed. *New Developments in Quantititative Coronary Angiography*, Kluwer Academic Publishers, 1988, pp. 225–247;

D. J. Hawkes, A. C. F. Colchester and C. R. Mol, "The Accurate 3D Reconstruction of the Geometric Configuration of the Vascular Trees from X-Ray Recordings" in R. Guzzardi ed. *Physics and Engineering of Medical Imaging*, Nijhoff, 1987;

M. Garreau, J-L Coatrieux, R. Collorec and C. Chardenon, "A Knowledge-Based Approach For 3D Reconstruction And Labelling Of Vascular Networks From Biplane Angiographic Projections" in *IEEE Medical Imaging*, Vol. 10, No. 2, June 1991, pp. 122–131.

This need for human intervention is a major drawback and may even become prohibitive in certain cases, when the number of viewpoints to be calibrated is large. This is especially so with any system for the acquisition of 2D projections by X-rays with a view to 3D reconstruction. A system of reconstruction such as this is described, for example, in the French patent application No. 2 644 590 filed on 20th Mar. 1989. Whatever the method of 3D reconstruction, it is necessary, first of all, to have perfect knowledge of the geometrical parameters that characterize each of the projections. In the probable case where an indirect calibration method is necessary, it would seem to be indispensable to carry out this calibration automatically.

The present invention therefore proposes a device enabling an automatic calibration that can be applied to any system of 2D X-ray imaging and in particular to any system used for purposes of 3D reconstruction.

The device of the invention is such that the unequivocal recognition of correspondences between the beads and their traces is automatic. This is obtained by choosing a phantom in which the beads are distributed, step by step or by degrees, in a sequence such that altitudes of beads, measured along the rotational axis of the imaging system and, especially, an axis of the phantom, are monotonically increasing (or decreasing) with an order number of the beads in the sequence.

SUMMARY OF THE INVENTION

To this end, an object of the invention, therefore, is to provide an X-ray imaging system with a 2D detector positioned so as to be facing an X-ray tube, this detector and this tube being capable, in certain cases, of rotating together about an axis, this X-ray imaging system comprising a geometrical calibration device provided with a phantom having known dimensions and with measuring means for deducing, from images of the phantom projected on the 2D detector, of the coefficients of calibration of this X-ray imaging system. The phantom comprises a step-by step succession of cellular structures having different levels, namely higher or lower levels, of radiological absorption as compared with their environment, each cellular structure being automatically identifiable by an ordered characteristic for the identification of this cellular structure.

Another problem to be resolved by the invention is related to the number of calibrations to be undertaken. A rotating imaging system of this type is indeed capable of applying 1000 or more angular positions on one rotation. Calibrations for all the angular positions, even when they are done automatically, are too lengthy to be capable of being repeated periodically, every week or every month. In fact, one workday has to be set aside for this purpose.

The method of the invention seeks to resolve this other problem by making the assumption that, although the theoretical dimensions of construction of the imaging system cannot be considered to have been met in the real system, it can nevertheless be assumed that the imaging system undergoes perfect circular rotation or almost perfect circular rotation. The idea of the method then is to seek the intrinsic parameters of the system: ultimately those parameters which, in addition, give the direction of its axis of rotation axis. From these intrinsic parameters, which can be known with very high precision, it is then possible to make a computation of calibration coefficients for each angular position. It is shown, for example, that about a hundred calibrations lead to very precise knowledge of these intrinsic parameters. With this knowledge, 900 other "calibrations" are computed. Then, a total of 1,000 calibrations are known, with only 100 having been measured. The gain in time is considerable.

Another object of the invention is to provide a method for the geometrical calibration of an X-ray imaging system with a 2D detector rotating about an axis, facing an X-ray tube, said method comprising the following steps:

a phantom of known dimensions is placed between the tube and the detector;

a measurement is made, for a rotational position of the tube/detector assembly with respect to the phantom, and in the radiological image of the phantom projected on the 2D detector, of the coordinates of image loci of characteristic points of the phantom;

a deducing is done, for this rotational position of the tube/detector assembly, and in a referential system associated with the position of the phantom, of the calibration coefficients pertaining to the respective positions of a focal spot of radiation from the X-ray tube and of the 2D detector;

and these last two steps are reiterated for different desired positions of the tube/detector assembly, wherein:

the calibration coefficients relating to a certain number of rotational positions of the tube/detector assembly are processed for the extraction therefrom of the intrinsic parameters of the X-ray imaging system which are independent of the rotational position of the tube/detector assembly;

and these intrinsic parameters are deduced from the calibration coefficients pertaining to any rotational position of the tube/detector assembly by assessing the values of analytic functions of these intrinsic parameters for an angular value of rotational position of the tube/detector assembly.

BRIEF DESCRIPTION OF THE DRAWINGS

The invention will be understood more clearly from the following description and from the figures that accompany it. These figures are given purely by way of an indication and in no way restrict the scope of the invention. Of these figures:

FIG. 1 shows an imaging system that can be used to implement the invention with the presentation of the different referential systems of acquisition;

FIGS. 2a to 2d respectively show a view in profile and a front view of the phantom according to the invention, the trace of the beads in the projections and a detailed view of the positioning of the beads being shown by overlay;

FIG. 3 shows the placing of the phantom in the imaging system;

FIGS. 4a and 4b show images in projection of a particular shape of the phantom after processing;

FIGS. 5a through 5d show geometrical representations that enable a better understanding of the method.

MORE DETAILED DESCRIPTION

FIG. 1 shows an imaging system that can be used to implement the invention. This system has an X-ray tube 1 with a radiation focal point or spot S. A radiation detector 2, for example of the luminance amplifier type used in radiology, is placed facing the tube 1. A line normal to the detection plane P of the detector 2 passes substantially through the focal spot S and the center I of detector 2. This may be necessary for the formation of conventional images but is not directly related to the problem of calibration. In particular, with the invention, it is possible to calibrate a homothetic translation type of tomograph. The system may rotate with a known type of mechanism (not shown) for tomodensitometers or with a bow, about an axis 3, which is herein shown vertically but is normally horizontal. In the case of tomographs, there are only translations and a homothetic center, without necessarily an axis. This is also the case, naturally, with static instruments. The system also comprises a processor 4 that subjects the electrical signals measured by the detector 2 to a processing operation contained in a program 2 stored in a program memory 6. Images, or statistical results got from these processing operations, may be displayed on a monitor 7.

The invention makes it possible to resolve the problem of the automatic recognition of the corresponding 2D/3D points by using, as a calibration phantom, a particularly well-suited phantom that is shown in FIGS. 2a to 2d and 3.

In one example, this phantom is a plexiglass cylinder used as a support for a series of small metal beads overlaid into the wall of the cylinder and positioned evenly in the form of a helix. The beads all have an identical diameter, for example 1 mm, except the middle bead, which has a greater diameter than the others, for example 3 mm. The parameters of the helix are roughly adapted to the image acquisition system so that its projection is as as great as possible on the detector while, at the same time, it remains contained in the image. Similarly, the helix pitch and the pitch for sampling the beads on the helix are chosen in such a way that a sufficient number of beads appears in the projection without superimposing. The dimensions in FIGS. 2a–2d, are given in millimeters. To prevent any deformation of the phantom 8, notably through the ageing of the plexiglass, the cylinder 8 is occluded on both sides by a lid 9 which ensures its rigidity.

The phantom 8 is adapted, for example, to an acquisition system constituted by an X-ray source and a round field detector with a diameter of 37 cm, located at a distance of about 135 cm from the focal spots, while the object is about 100 cm from the focal spot S. These figures are examples that in no way restrict the scope of the invention, as also are the dimensions of the phantom that are appended hereto. In the example, there are 61 beads. One of the coordinates of the beads, the altitude measured on a longitudinal axis Z, changes from one bead to the next one in 5-mm steps with a precision of 5/100ths. There are 20 evenly distributed beads per turn of the helix.

The following are the three main particular features of the phantom 8. First of all, the phantom 8 has a sufficient number of beads for the calibration. They are well distributed in the 3D space. Their projections are also well distributed in the plane P (which is the indispensable condition for a 3D calibration). However, the evenness of the distribution is not essential. To this end, the beads can easily be numbered as a function of their dimension along the Z axis. This is obtained here according to a very simple formula:

$z = h.n + z0$,
$z$ = coordinates along Z,
$z0$ = coordinate of the bead No. 0,
$h$ = sampling pitch of the beads along Z,
$n$ = bead number.

It is in fact the order relation or ordering that is important to us here:

if $z1 > z2$, then $n1 > n2$ $z1, z2$ = coordinates of the beads 1 and 2 along Z $n1$, $n2$ = bead numbers.

If the phantom is positioned judiciously before the X-ray detector, i.e. essentially in such a way that the Z axis is roughly parallel to the plane P of the detector 2, and if the conicity of the beam is not too great, this order relation is also found in the 2D projections.

Indeed, referring to FIG. 3, let V be the axis in the projection plane P that corresponds to the projection of the Z axis. There will be the following relationship:

if $v1 > v2$, then $n1 > n2$ $v1, v2$ = coordinates of the beads 1 and 2 along V $n1$, $n2$ = bead numbers.

Hereinafter, and with a view to simplicity, it will be assumed that the V axis coincides substantially with the vertical axis in the images of projection, i.e. that it is parallel to the columns of the image. If this is not so, a rotation may be introduced into the projection plane to arrive at this condition.

Again with a view to simplicity here below, the referential system in the 3D space is defined as being related to the helix, i.e. the Z axis of the helix defines one of the axes of the referential system R, the other two axes being perpendicular to Z. In this referential system, the coordinates of the beads are expressed very easily. This means that, once the calibration is done, the system has a vertical axis which is the one that was occupied by the axis of the phantom during the calibration. 3D reconstructions pertaining to different calibrations are therefore not directly comparable. This will be possible, on the contrary, with the method of the invention seen further below. FIG. 3 shows the phantom 8 positioned between the X-ray source S and the X-ray detector D. The phantom is positioned in such a way that its main axis, the Z axis, is roughly parallel to the plane P, and in such a way that it is projected along the V axis of the detector.

Finally, the numbering of the beads can be done in an absolute way. Even if the top and the bottom of the projection of the helix are truncated (i.e. neither the first bead nor the last bead of the phantom is seen), we have an absolute reference which is the special, large, middle bead. The special bead, or two special beads, or others, are preferably placed in the phantom at a place which will, in all likelihood, be in the field: in the middle of the phantom.

For an understanding of the principle implemented in the calibration method, a description has been given, in the foregoing paragraphs, of a particular example of a phantom that meets the criteria described. In fact, any phantom having the following particular features would enable an automatic calibration. These particular features are:

the phantom must have cellular structures, beads to simplify the description, that are visible in X-rays, and are well distributed in the 3D space. Their radiological contrast in relation to their environment needs to be high. The projections of the beads must be contained in the 3D image at least for the central beads. It is not at all necessary for the support of the beads to be a hollow plexiglass cylinder.

there must be an ordering or order relation between a number that can be assigned to the beads and their coordinates, in the 3D space along the Z axis as well as in the projection along an axis, for example the V axis, irrespectively of the orientation of the phantom in the apparatus. The axis of the phantom must be substantially parallel to the plane of the detector. The approach using beads that are evenly distributed on a helix as in the particular case of the phantom that is described, is not at all the only one; it must be possible to recognize at least one of the beads among the others, so as to enable an absolute numbering even if the first bead and the last bead in the projection are not seen. This reference bead may be distinguished by a factor other than its diameter, for example its shape, its opacity to X-rays, its absence or again an unevenness in the distribution pitch or any other criterion.

For example, we may cite another possible embodiment for the phantom: the beads are distributed on a "degenerate" helix which is borne by a plexiglass sphere instead of being borne by a cylinder. Hereinafter, the reasoning shall be based on the preferred "helical" phantom as described here above. The entire method explained here below can also be applied with another method meeting the criteria.

A description is given here below of the sequence of the operations to be carried out in order to calibrate the system.

1. The phantom 8 described here above is positioned in such a way that its main axis (Z axis) is somewhat parallel to the plane of the detector. This is the case, for example, when it is positioned so as to be laid on an examination table of an angiographic system, and when the bow that bears the X-ray tube and the detector is positioned in a plane perpendicular to the table. In this position, the projections of the beads verify the above order relation.
2. A digitized projection of the phantom is acquired under the conditions of incidence that are to be calibrated;
3. The image is transferred to the image processor 4;
4. The image is corrected for possible geometrical distortions, for example with a method such as the one described in the French patent application No. 2 633 793 filed on 1st Jul. 1988;
5. The corrected image I is then subjected to an algorithm for the detection, localization and automatic labelling of the beads described hereinafter;
6. The coordinates of the beads in the 3D referential system R and the coordinates of their projections in the 2D referential system of the plane P are exploited to estimate the geometrical parameters of the projection: the calibration coefficients. An algorithm based on a minimization of error by the technique of the conjugate gradient is proposed and is also described here below to this end.

Herein, a description is given of a possible exemplary calibration algorithm which makes it possible to go from the projected image of the calibration phantom (FIG. 4a–image I) to intrinsic geometrical parameters of the machine. Throughout this description, we shall show the images resulting from the different processing operations.

1. First of all, the image I is segmented. The aim here is to eliminate from the image I, the signal of the projection of the plexiglass cylinder that supports the beads. To this end, tools of mathematical morphology are used such as a top-hat transformation with a round-shaped structuring element having a size greater than the size of the beads in the image I. A signal S1 is obtained, containing nothing more than the signal corresponding to the absorption of the beads. The tools of mathematical morphology are of a known type and have been published in many works.
2. The image S1 needs to be rid of residual artefacts coming from the edges of the cylinder. To this end, once again, a transformation of mathematical morphology is used, aimed at eliminating the vertical structures in the image. The resulting image is an image S2 that can be seen in FIG. 4b in negative. The image S2 therefore contains all the beads (positive signal) on a background with zero value, apart from the noise.
3. The image S2 is then segmented. The aim here is to keep only the signal coming from the large central bead of the phantom. For this purpose, use is made of an erosion of the image S2 or a removal of all images having a size greater than the size of the small beads but smaller than the size of the large bead. There is obtained an image S3 that contains only the large bead.
4. All of the beads in the image S2 are then detected. It is sought here to localize the projections of all the beads in the image to the nearest pixel. The operation starts with the line 0 of the image (at the top of the detector). The entire image is crossed from the top to the bottom. A positive signal encountered in the image is declared to be a bead if this signal is above a certain threshold 1. The number 0 is given to the first bead encountered, then the number is incremented at each bead encountered, until the bottom of the image. It is certain that the order of the numbers is the right one, owing to the properties of the helix described here above.
5. A computation is then made of the exact coordinates of each of the beads. The aim here is to know the coordinates of each of the beads in the image, with sub-pixel precision. For each bead in the image S2, a computation is made of the center of gravity in terms of gray levels of the set of pixels around the detected bead, such that their gray level is higher than a second threshold, threshold T2 (threshold T2<threshold T1). A computation of this type is undertaken, for example, in the second French patent application referred to here above. Its principle is based on the fact that the beads are fine enough so as not to absorb all of the X-radiation. Then, when there is no absorption saturation, a pixel is obtained.
6. The large bead is then detected in the image S3; its coordinates are then known to the nearest pixel. Its coordinates are compared with those of all the beads detected in the image S2 and thus, in the list of all the beads, the largest bead is recognized.
7. Since the largest bead is recognized in the projection, it is now possible to renumber all of the beads in an absolute way and thus be sure of an exact correspondence, for each bead, between its number and its 3D coordinates, which are known besides, and the 2D coordinates of its projection.

With the 3D coordinates and the 2D coordinates of its projection being known for each bead, it is possible to compute the reprojection error associated with a choice of arbitrary values for the nine parameters of the conical projection. This error is obtained by the difference between the position computed with these arbitrary values and the position found in the image of the calibration phantom. It is therefore possible to estimate the parameters or calibration coefficients associated with the viewpoint, i.e. with the rotational position, that is to be calibrated, by choosing the parameters that minimize a reprojection error criterion for all the beads detected.

The proposed parameter estimation algorithm uses the conjugate gradient minimization technique applied to the mean square error criterion. This standard technique necessitates the computation of the criterion and of its prime derivatives as a function of the parameters. This algorithm has been published by W. H. Press, B. P. Flannery, S. A. Teukolsky and W. T. Vetterling in Numerical Recipes in C, Cambridge University Press, 1988, ch. 10.6, pp. 317 & ff. Other algorithms, called Simplex and Newton and described in the same pages in this work, could also be used. The first one, Simplex, has the advantage of being adaptable to any coherent system of parametrization. However, it does not converge rapidly. The algorithm of the conjugate gradient converges more quickly but calls for a choice of parametrization such that the analytic expressions of the parameters are derivable. This is the case with the parametrization described here above. The computations pertaining to this algorithm have been presented to the Congress on "3D Advanced Imaging Processing In Medecine", Rennes, France during the 14th annual IEEE EMBS annual conference from 2 to 4 Nov. 1992 by Anne Rougee, Catherine Picard, Cyril Ponchut and Yves Trousset.

The following are the steps in this algorithm:
1. Initialization: the parameters have to be initialized at realistic values. This makes it possible to launch the minimization in a region close to the solution.
2. Standardization: around this initial value, it is possible to compute the value of a criterion corresponding to a shift by one unit on each axis of the space of the parameters, and then to carry out a change of variable in this space by changing the scale on each axis so that any shift by one unit on each axis prompts the same effect on the criterion.
3. Minimization: starting from the initial value, and taking account of a change in scale found during the standardization step, the iterative technique of the conjugate gradient is applied to minimize the mean square error on all the beads detected. At each iteration, a new estimation of the parameters is computed as a function of the derivatives of the criterion. The process is stopped when the relative divergence between the current estimation and the next one is below a given threshold.

The term "3D reconstruction machine" is applied to a machine that carries out radiographies of an object at different angles of incidence obtained by rotation about an axis. These radiographies are then used to reconstruct 3D information. This machine can be built, for example, on the basis of a rigid ring on which the tube/detector assembly rotates, in which case the rotational axis is fixed and never changes in the course of time. Or else, it may built as a structure based on a tilting stand that supports the tube/detector assembly, in which case the axis of rotation may be positioned in different ways in space.

Rather than computing the parameters called calibration coefficients for each viewpoint, namely for each rotational position, of the tube/detector assembly, it is possible, according to one method of the invention, to compute intrinsic parameters of the rotating system. These instrinsic parameters are then analytic functions of the rotational position of the rotating assembly. To obtain the calibration parameters pertaining to a position, it is then enough to compute the value of the intrinsic parameters for a given value of orientation of the rotating system. Already, the prior art systems normally deliver a measurement, most usually in the form of an electrical signal, representing their orientation in space. It enough to use this measurement to obtain the calibration coefficients pertaining to this orientation by carrying the measurement into the analytic expressions of the intrinsic parameters.

To estimate the instrinsic parameters describing the overall geometry of a 3D reconstruction machine in condensed form, the following procedure may be used: an estimation is made of the parameters of the conical projection, view by view, during a first step and then the intrinsic parameters are estimated on the basis of these parameters during a second step.

First Step

In the case of a 3D reconstruction machine, the method of automatic calibration is particularly well suited to estimating the calibration coefficients, view by view, in the course of a rotation.

The helix is positioned on the examination table with its Z axis approximately centered on the rotational axis of the machine. For each of the viewpoints of acquisition of a machine during a rotation, the projection of the helix will be obtained, and thus all the acquired images will be processed, with the method described here above.

The proposed parametrization (with cylindrical 3D coordinates) is suited to estimating the parameters along a circular trajectory about the Z axis. The initialization and standardization steps are carried out for the first view only. The values of the parameters found for the first view are then used to initialize the estimation of the parameters of the next view, and so on and so forth, until the last view. This enables the computations to be accelerated.

Thus, the geometrical parameters for each viewpoint are obtained. These geometrical parameters are stored in the digital disk of the machine, and will be used in every 3D reconstruction step.

Second Step

It is possible, according to the invention, to pass from knowledge of the calibration coefficients, view by view, to knowledge of instrinsic parameters that describe the overall geometry of the machine in condensed form.

Let N be the number of calibrated viewpoints. For example, N=100. Should each viewpoint be calibrated independently of its neighbor, there are 9N parameters available to describe the geometry of the acquisitions. Now, in the case of a system where the tube and detector are linked, where this system rotates about a fixed axis, it can be seen that these 9N parameters are redundant. The geometry of acquisition of the 3D reconstruction machine can parametrized with a far larger number of parameters which are, preferably:
the coordinates of an isocenter O of the system (3 parameters);
the direction of the Z' axis of rotation passing through the isocenter O. It is given by two angles (two parameters);
the radii $r_I$ and $r_S$ of the trajectories of I and of the source S (two parameters);
the difference in dimension (along the Z' axis of rotation) between the trajectory of the source and that of I (1 parameter);

the angular difference ε between the polar angle of S with respect to Z' and the polar angle of I with respect to Z' (one parameter);

the two tilts $\alpha_1$ and $\alpha_2$ of the detector, the angles of orientation of the detector with respect to the Z' axis (2 parameters);

the angle $\alpha_3$ between the columns of the image and the projection of the Z' axis in the image (1 parameter).

There is thus a total of 12 parameters obtained. Other choices for these 12 parameters are possible. This particular choice is preferred for reasons similar to the foregoing ones, namely the simplification of the computations. It will be noted that, in this case, the referential system in which the values of these intrinsic parameters is expressed is independent of the position of the phantom. It can therefore be transposed from one calibration to the other. One method to estimate these 12 parameters as a function of the 9N initial parameters may be, for example, the following one:

1. Finding the direction of the Z' axis of rotation:

The N points $I_n$ (n−1, N) forming the trajectory of I are considered. In theory, this trajectory is plane and orthogonal to Z'. Hence the closest plane, in terms of the least squares, to the set of points $I_n$ is sought, and the direction of Z', which is the normal to this plane, is deduced therefrom.

Let $(X_n Y_n Z_n)$ be the coordinates of a point $I_n$. The plane of equation $z = ax + by + c$ which is the "closest" to the set of the points $I_n$ is sought. The distance between the plane $z = ax + by + c$ and the set of the points $I_n$ is called $d(a,b,c)$. The coefficients $(a,b,c)$ that minimize the distance $d(a,b,c)$ are sought.

$$d(a,b,c) = \Sigma(ax_n + by_n + c - z_n)^2$$

is defined, and then it is very easy to find the triplet $(a,b,c)$ which minimizes $d(a,b,c)$ by linear regression.

2. Finding the coordinates of the isocenter, and the radius of the trajectory of I:

The isocenter is the center of both the trajectory of I and the trajectory of S. This center will therefore be sought by analyzing the trajectory of I.

Note: in this step, the parameters (center and radius) of the trajectory of I are sought and then, in the next step, the radius of the trajectory of S is sought. It could have been possible, quite logically, to do the opposite, namely to start by seeking the center and radius of the trajectory of S and then to deduce the radius and the trajectory of I therefrom. This approach is however less robust than the one explained herein. This is because, since the point S is further away from the rotational axis than the point I, the information elements on the position of S are far more error-ridden than those on the position of I. It is therefore the "definite" information elements (those on I) that are used as the basis of the method and not those on S, which are more uncertain. Another approach would also consist in finding the radii and centers of the trajectories of I and S simultaneously. For the same reasons of robustness, this method has not been chosen.

What is the way to find the coordinates of the isocenter, i.e. those of the center of the trajectory of I? A plane is defined as being orthogonal to Z' and as having one dimension along Z' equal to the mean of the dimensions of the points $I_n$. All the points $I_n$ are projected orthogonally to this plane at points $I'_n$. Since the trajectory of I is assumed to be circular, the points $I'_n$ are located, in principle, on a circle. Then the circle that is closest, in terms of the least squares, to the set of the points $I'_n$ is sought, which gives us:

the radius $r_1$ of the trajectory of I (i.e. the radius of the circle found), the coordinates of the isocenter, which is herein defined as the intersection of π and of the rotational axis (it is actually the center of the circle that was found).

What is the way to define and find the closest circle? Let $C(A,r)$ be a circle with a center A and a radius r. What must be done is to define a distance $d(A,r)$ between the circle $C(A,r)$ and the set of points $I'_n$. Several methods are possible:

Method 1—FIG. 5a

Let $(x'_n, Y'_n)$ be the coordinates of $I'_n$. The following is defined: $d(A,r) = \Sigma I'_n J'_n$, the point $J'_n$ being defined as the intersection of the circle $C(A,r)$p and of the straight line $AI'_n$.

Method 2—FIG. 5b

When the 3D reconstruction machine shoots X-rays according to regular angular positions, i.e. every δΘ degrees (δΘ constant), this knowledge can be used to obtain greater robustness in the determination of the parameters of the circle.

$d(A,r)$ shall be defined by: $d(A,r) = \Sigma I'_n J'_n$, the point $J'_n$ being defined this time as the point of the circle $C(A,r)$ which, with respect to a reference direction, possesses an polar angle: $\Theta = \Theta_0 + (n-1)^* \delta\Theta$.

Whether it is the method 1 or the method 2 that is adopted to define the distance between the circle and the cloud of points, the rest of the procedure is the same: any method of minimization (conjugate gradient method for example) is used to seek the parameters A and r of the circle (or, in the method 2, the parameters a, r and $\Theta_0$) which minimize the distance to the circle. Once these parameters are found, the procedure is over since:

the radius of the trajectory of J is known: it is r;
   the axis Z' of rotation is entirely known, since its orientation has been determined at the previous step and since it is now known that this axis passes through A.

3. Finding the radius of the trajectory of S.

The center of the trajectory of S is known since, by definition, it is the same as that of the trajectory of I which has just been found in the previous step. The radius can now be sought The points $S'_n$, which are projections of the points s on the plane π are considered. The radius of the trajectory of S is defined as the mean of the distances between the isocenter O and the points $S'_n$:

radius of $I = 1/N^* \Sigma OS'_n$

4. Finding the difference in dimension along the axis Z' between the trajectory of the source and that of I.

This is the mean of the dimensions along the axis Z' of the points $S_n$ (see FIG. 5c). The difference in dimension is deduced therefrom by the distance to the plane π.

5. Finding the angle ε.

The operation uses the projections I' and $S'_n$ in the plane π. For each n, the polar angles (with respect to 0) of $I'_n$ and $S'_n$ are computed and their difference (see FIG. 5d) is called $\varepsilon_n$. ε is estimated as being the mean of the values $\varepsilon_n$.

6. Finding the tilts $\alpha_1$ and $\alpha_2$ of the detector.

For each view, a computation is made, in the referential system related to the axis of the helix, of the coordinates of the normal to the detector. Then, by the application of a formula for changing the referential system between the referential system related to the axis of the helix and the referential system related to the isocenter and to the axis of rotation Z', a deduction is made of the coordinates of the normal to the detector in the referential system related to the isocenter and to the Z' axis of rotation. This referential-changing formula is deduced from the knowledge of the referential system related to the helix. Furthermore, the isocenter is known since it is the center of the circle found here above. The orientation of the Z' axis is also known. The other two axes of this referential system are fixed, except for one rotation. Preferably, in order to fix them, it is seen to it that, in the new referential system, the first view is assigned an angle $\Theta_0$ related to a preferred position of the machine. In this new reference, these coordinates depend only on the two angles $\alpha_1$ and $\alpha_2$. For each n, these two angles referenced $\alpha_{1n}$ and $\alpha_{2n}$ are computed. Then $\alpha_1$ is defined as the mean of the values of $\alpha_{1n}$ and the same is done for $\alpha_{2n}$.

Finding the angle $\alpha_3$.

For each view, a computation is made, in the referential system related to the axis of the helix, of the coordinates of the unit vector parallel to the columns of the detector. Then, by application of the referential-changing formula, its coordinates are deduced in the referential system related to the isocenter and to the Z' axis of rotation. Now, in this new referential system, these coordinates depend only on the angle $\alpha_3$. For each n, this angle, referenced $\alpha_{3n}$, is computed. Then $\alpha_3$ is defined as the mean of values of $\alpha_{3n}$.

Third Step

There are now 12 intrinsic parameters known, defining the geometry of the system. On the basis of the knowledge of these 12 intrinsic parameters, it is very easy to make a recomputation, for each view n, of the 9 local calibration parameters defining this view. This computation is all the simpler as it takes place in the intrinsic referential system of the machine, i.e. in the referential system related to the isocenter and to the axis of rotation. The 9 local parameters relating to the view n, as defined in the paper published at the Rennes Congress, are called ($rs_n$, $as_n$, $zs_n$, $theta_n$, $phi_n$, $psi_n$, $ri_n$, $ai_n$, $zi_n$). We then get:

$rs_n$ = radius of the trajectory of the source (=constant);

$as_n = \Theta_0 + 180 + (n-1) * \delta\Theta$ $zs_n$ = difference in dimension computed here above (=constant);

$theta_n = \Theta_{0+(n-1)} * \delta\Theta + \alpha 1$ $phi_n = \alpha 2$ $psi_n = \alpha 3$ $ri_n$ = radius of the trajectory of S (=constant)

$ai_n = \Theta_0 + (n-1) * \delta\Theta$ $zi_n = 0$ (=constant)

These nine calibration coefficients or parameters are therefore determined on the basis of the incidence deduced from $\Theta_0 + (n-1) \delta\Theta$. They are known with great precision in view of the statistical evaluations from which they result. With precise measurements of the incidence, therefore, we arrive at computed coefficients of calibration that are very precise. The incidence itself is deduced from the index n. This index is known by the division of the circumference of the machine into a given number of preset positions.

It will be noted that, preferably, a recomputation will be made, on the basis of the analytical expressions according to the intrinsic coefficients, of the calibration coefficients relating to the N views calibrated. Consequently, the calibration coefficients for these N (100) views are assessed with as much precision as for the other views (the 900 other views). The overall result is even better.

Another possible method would consist of making a direct estimation of the global parameters of the machine on the basis of all the coordinates of the beads detected in all the projections of the helix. However, this method is a lengthy one.

What is claimed is:

1. A rotating system for 3D X-ray imaging, comprising: a 2D detector positioned so as to be facing an X-ray tube, the 2D detector and X-ray tube being rotatable about a common axis; and a geometrical calibration device provided with (1) a 3D phantom having known dimensions and with (2) measuring means for deducing, from images of the phantom projected on the 2D detector, the calibration coefficients of this X-ray imaging system, wherein the phantom has an axis and comprises a step-by-step succession of cellular structure with radiological absorption that is contrasted with respect to their environment, each cellular structure being automatically identifiable by an ordered characteristic for the identification of this cellular structure, this being the case for all the positions, in rotation, of the system, the axis of the phantom being designed to be oriented in the X-ray imaging system, in a calibration phase, substantially in parallel to a plane of the 2D detector.

2. An X-ray imaging system according to claim 1, wherein the ordered characteristic for the identification of each cellular structure comprises referencing this cellular structure with respect to at least one particular cellular structure of the phantom.

3. An X-ray imaging system according to claim 1, wherein the cellular structures possess radiological absorption levels that are insufficient for the total prevention of the passage of the X-radiation through them.

4. An X-ray imaging system according to claim 1, wherein the cellular structures comprise metal beads placed at the bottom of wells made in a support.

5. An X-ray imaging system as defined in claim 1, wherein one of said cellular structures is a reference structure which is radiologically distinguishable from the remaining cellular structures, the remaining cellular structures being radiologically indistinguishable from one another.

6. An X-ray imaging system as defined in claim 5, wherein said reference structure is larger than the remaining cellular structures and the remaining cellular structures are of uniform size.

7. An X-ray imaging system comprising: a 2D detector positioned so as to be facing an X-ray tube, the 2D detector and X-ray tube being rotatable about a common axis; and a geometrical calibration device provided with (1) a 3D phantom having known dimensions and with (2) measuring means for deducing, from images of the phantom projected on the 2D detector, the calibration coefficients of this X-ray imaging system, wherein the phantom comprises a step-by-step succession of cellular structure with radiological absorption that is contrasted with respect to their environment, each cellular structure being automatically identifiable by an ordered characteristic for the identification of this cellular structure, this being the case for all the positions, in rotation, of the systems, wherein the phantom also has an axis, a support, and a distribution of the cellular structures on this support, in such a way that these cellular structures, measured along this axis of the phantom, are monotonic and increasing with an order number of these cellular structures, the axis of the phantom being designed to be oriented in the X-ray imaging system, in a calibration phase, substantially in parallel to the axis of this X-ray imaging system, and in such a way that this ordering is found again in the projection of the phantom.

8. An X-ray imaging system according to claim 7, wherein the support is a circular cylinder whose generatrices are parallel to the axis of this cylinder, and wherein the ordered succession of the cellular structures on this support is shaped substantially like a helix.

9. An X-ray imaging system according to claim 8, wherein the cylindrical support is provided, at its ends, with steadying plates to prevent its deformation.

10. An X-ray imaging system comprising: a 2D detector positioned so as to be facing an X-ray tube, the 2D detector and X-ray tube being rotatable about a common axis; and a geometrical calibration device provided with (1) a 3D phantom having known dimensions and with (2) measuring means for deducing, from images of the phantom projected on the 2D detector, the calibration coefficients of this X-ray imaging system, wherein the phantom comprises a step-by-step succession of cellular structure with radiological absorption that is contrasted with respect to their environment, each cellular structure being automatically identifiable by an ordered characteristic for the identification of this cellular structure, this being the case for all the positions, in rotation, of the system, wherein the ordered characteristic for the identification of each cellular structure comprises referencing this cellular structure with respect to at least one particular cellular structure of the phantom, and wherein a particular cellular structure of the phantom has a size or a radiological absorption which is different from that of the other cellular structures and is placed substantially in the middle of the distribution of the cellular structures.

11. A method for the geometrical calibration of an X-ray imaging system with a 2D detector rotating about an axis, facing an X-ray tube, said method comprising the following steps:
placing a phantom of known dimensions between the tube and the detector;
measuring, for a rotational position of the tube/detector assembly with respect to the phantom, in the radiological image of the phantom projected on the 2D detector, the coordinates of image loci of characteristic points of the phantom;
deducing for this rotational position of the tube/detector assembly, and in a referential system associated with the position of the phantom, the calibration coefficients pertaining to the respective positions of a focal spot of radiation from the X-ray tube and of the 2D detector;
reiterating the measuring and deducing steps for different desired positions of the tube/detector assembly, wherein:
the calibration coefficients relating to a certain number of rotational positions of the tube/detector assembly are processed for the extraction therefrom of the intrinsic parameters of the X-ray imaging system which are independent of the rotational position of the tube/detector assembly;
and these intrinsic parameters are deduced from the calibration coefficients pertaining to any rotational position of the tube/detector assembly by assessing the values of analytic functions of these intrinsic parameters for an angular value of rotational position of the tube/detector assembly.

12. A method according to claim 11, wherein: in order to deduce calibration coefficients relating to a desired rotational position of the tube/detector assembly:
a) a simulation is done, with calibration coefficients deduced from the mechanical construction of the X-ray imaging system,
b) the coordinates of these theoretical loci are compared with those of the loci measured in the image of the phantom,
c) the calibration coefficients are modified in correspondence,
d) and the two steps a) and b) are reiterated until the comparison shows a negligible difference, in which case the last calibration coefficients modified are chosen as the calibration coefficient for this rotational position of the tube/detector assembly.

13. A method according to claim 11, wherein calibration functions are expressed by analytical functions of the intrinsic parameters, these analytical functions being described in a cylindrical referential system.

14. A method according to claim 11, wherein the intrinsic parameters are obtained, by statistical evaluation, from a limited number of images of the phantom, for various orientations of the imaging system.

15. A method according to claim 11, wherein intrinsic parameters are used as the basis for deducing calibration coefficients relating to rotational positions of the tube/detector assembly for which measurements have been made of the coordinates of image loci of characteristic points of the phantom, and for which calibration coefficients had been deduced.

16. A method according to claim 1, wherein, in order to deduce calibration coefficients relating to a desired rotational position of the tube/detector assembly:
a) a simulation is done, with arbitrary calibration coefficients, of the coordinates of theoretical loci that are images, on the 2D detector, of characteristic points of the phantom,
b) the coordinates of these theoretical loci are compared with those of the loci measured in the image of the phantom,
c) the arbitrary calibration coefficients are modified in correspondence,
d) and the two steps a) and b) are reiterated until the comparison shows a negligible difference, in which case the last calibration coefficients modified are chosen as the calibration coefficient for this rotational position of the tube/detector assembly.

17. A method according to claim 16, wherein:
to deduce calibration coefficients relating to a desired new rotational position of the tube/detector assembly, this new position being offset with respect to a preceding rotational position, instead of using the arbitrary calibration coefficients relating to this new rotational position, the last modified coefficients obtained for this preceding rotational position are used.

18. An X-ray imaging system comprising:
an X-ray tube and a 2D detector rotatable about a common axis to form a tube/detector assembly, said detector facing said X-ray tube; and
a geometrical calibration device including (1) a 3D phantom and (2) measuring means for deducing calibration coefficients of said system from images of said phantom projected onto said 2D detector, wherein said phantom has known dimensions, has an axis which, in a calibration phase, is designed to be orientated in the system substantially in parallel to the plane of said detector, and comprises a succession of cellular structures, each said cellular structure (1) having radiological adsorption characteristics different from those of the surrounding environment and (2) being automatically identifiable by an ordered characteristic for identification in all rotational positions of said tube/detector assembly.

19. An X-ray imaging system as defined in claim 18, wherein (1), in said calibration phase, said axis of said phantom is substantially parallel to said common axis, and (2) said phantom further comprises a support in which said cellular structures are distributed in such a way that they are monotonic and increase with an order number when measured along the axis of said phantom.

20. A method of calibrating an X-ray imaging system, comprising:
providing an X-ray imaging system including an X-ray tube and a 2D detector which faces said X-ray tube, said X-ray tube and said detector forming a tube/detector assembly which is rotatable about an axis;

placing a phantom of known dimensions between said X-ray tube and said detector;

projecting a radiological image of said phantom onto said detector;

measuring the coordinates of image loci of characteristic radiological points of said image of said phantom for a rotational position of said tube/detector assembly;

deducing, for said rotational position of said tube/detector assembly, calibration coefficients pertaining to the respective positions of (1) a focal spot of radiation from said X-ray tube and of (2) said detector; and reiterating the measuring and deducing steps for different desired rotational positions of said tube/detector assembly.

21. A method as defined in claim 20, wherein
intrinsic parameters of said system are extracted from the calibration coefficients relating to a certain number of rotational positions of said tube/detector assembly, said intrinsic parameters being independent of the rotational position of said tube/detector assembly; and wherein said intrinsic parameters are deduced from the calibration coefficients pertaining to any rotational position of said tube/detector assembly by assessing the values of the analytic functions of said intrinsic parameters for an angular value of rotational position of said tube/detector assembly.

22. A method as defined in claim 20, wherein said step of placing a phantom comprises placing a phantom which comprises a succession of cellular structures, each said cellular structure (1) having radiological adsorption characteristics different from those of the surrounding environment and (2) being automatically identifiable by an ordered characteristic for identification in all rotational positions of said tube/detector assembly.

23. A method as defined in claim 20, wherein said step of placing a phantom comprises placing a phantom having an axis which, in a calibration phase, is designed to be orientated in the system substantially in parallel to the plane of said detector.

* * * * *